United States Patent [19]
Berkcan

[11] Patent Number: 5,343,037
[45] Date of Patent: Aug. 30, 1994

[54] ENVIRONMENTAL AND PHYSICAL PARAMETER SENSORS INCORPORATING POLYMER-COVERED FIBER FIELD ACCESS BLOCKS

[75] Inventor: Ertugrul Berkcan, Niskayuna, N.Y.

[73] Assignee: General Electric Company, Schenectady, N.Y.

[21] Appl. No.: 79,764

[22] Filed: Jun. 21, 1993

[51] Int. Cl.$^5$ .............................................. H01J 5/16
[52] U.S. Cl. ............................ 250/227.21; 250/227.18
[58] Field of Search ....................... 250/227.18, 227.14, 250/227.16, 227.23, 227.25; 385/12, 13

[56] References Cited

U.S. PATENT DOCUMENTS

| | | | |
|---|---|---|---|
| 4,560,248 | 12/1985 | Cramp et al. | 385/12 |
| 4,710,353 | 12/1987 | Tanaka et al. | 385/12 |
| 4,758,087 | 7/1988 | Hicks, Jr. | 250/227.18 |
| 4,795,226 | 1/1989 | Bennion et al. | 385/12 |
| 4,815,843 | 3/1989 | Tiefenthaler et al. | 385/12 |
| 4,834,496 | 5/1989 | Blyler et al. | 250/227.18 |
| 4,842,783 | 6/1989 | Blaylock | 385/12 |
| 4,894,532 | 1/1990 | Peterson et al. | 250/227.23 |
| 5,007,705 | 4/1991 | Morey et al. | 385/12 |
| 5,138,153 | 8/1992 | Gergely et al. | 250/227.18 |

OTHER PUBLICATIONS

"Narrow-band Bragg Reflectors in Optical Fibers," B. S. Kawasaki, et al, Optics Letters, vol. 3, No. 2, Aug. 1978, pp. 66-68.
"Formation of Bragg gratings in optical fibers by a transverse holographic method", G. Meltz, et al, Optics Letters, vol. 14, No. 15, Aug. 1989, pp. 823-825.
"Grating-fiber Coupler as a High-Resolution Spectrometer", by P. St. J. Russell et al, vol. 10, No. 6, Jun. 1985, Optics Letter, pp. 291-293.
"Deformation Recording Media", Encyclopedia of Chemical Technology, vol. 7, 3rd Edition, pp. 448-461, 1979.
"A Single-Mode Fiber Evansescent Grating Reflector", By W. V. Sorin, et al, Journal Lightwave Technology, vol. LT-3, No. 5, Oct. 1985, pp. 1041-1043.
"Flory-Huggins Theory" [163,164], ISBN 0-387-507-77-9 Polymers, 1990, pp. 161-165.
"High-Reflectivity Monomode-Fibre Grating Filters", by I. Bennion, et al, Electronic Letters, vol. 22, No. 6, Mar. 1986, pp. 341-343.
"Fiber Bragg Grating Chemical Sensor", by G. Meltz, et al, SPIE, vol. 1587, 1991, pp. 350-361.
"Photocharge Process", by J. Gaynor, et al, Photographic Science and Engineering, vol. 11, No. 3, 1967, pp. 204-211.
"A Novel Fibre Refractive Index Sensor Using Resonance Shift Phenomena", G. Thursby, et al, 8th Fiber Sensors Conference, Jan. 1992.
"Light Waves in Thin films and Integrated Optics", P. K. Tien, Applied Optics, vol. 190, No. 11, Nov. 1971.
"Exposed-core Single-Mode-Fiber Channel-Dropping Filter Using a High-Index Overlay Waveguide", C. A. Millar, et al, Optics Letters, vol. 12, No. 4, Apr. 1987.

Primary Examiner—David C. Nelms
Attorney, Agent, or Firm—Ann M. Kratz; Marvin Snyder

[57] ABSTRACT

An apparatus for detecting presence of a measurand includes a measurand sensitive layer overlying a fiber field access block. The fiber field access block has a clad fiber positioned such that a portion of the fiber is exposed to the measurand sensitive layer and any cladding on that portion of the fiber is thinner than required to prevent an evanescent wave from escaping the fiber. An optical source and an optical detection component are coupled to the fiber. Changes in the measurand sensitive layer, which are caused by interaction with the measurand, alter the phase velocity matching conditions of the fiber and measurand sensitive layer and can be measured by evaluating shifts in the output signals resulting from presence of the measurand.

18 Claims, 5 Drawing Sheets

ENVIRONMENTAL AND PHYSICAL PARAMETER SENSORS INCORPORATING POLYMER-COVERED FIBER FIELD ACCESS BLOCKS

CROSS-REFERENCE TO RELATED APPLICATION

This application is related to the following co-pending application which is commonly assigned and is incorporated herein by reference: Berkcan, "High Accuracy and High Sensitivity Environmental Fiber Optic Sensor", Ser. No. 08/079,763, filed concurrently herewith.

BACKGROUND OF THE INVENTION

1. Field of the Invention

This invention relates generally to sensors, and, more particularly, to sensors of various analytes fabricated by positioning on a fiber field access block a measurand sensitive waveguide whose properties are changed as a result of interactions with the environment.

2. Description of the Related Art

One conventional device for detecting the presence of analytes is an extrinsic polymer swelling sensor that uses reflections from a surface which is moved by the swelling of the polymer to provide an indication of the concentration of analytes. This type of sensor cannot be protected from the effects of temperature and is vulnerable to vibrations, pressure changes, and contaminants that may exist in the analyte.

Several other fiber optic chemical sensors rely on conventional spectroscopic instrumentation. In these cases the detector is usually a photomultiplier tube or a photodiode. The sources are usually a tungsten-halogen lamp, a xenon arc lamp, or an argon ion laser. These types of sensors require sophisticated, miniaturized demodulation equipment.

Other attempts have been made to use sensors to exploit properties of fiber optic media to transport light between a sample and the light source or detector. These techniques use light wavelengths in the blue or ultraviolet range in order to be sensitive to the spectral characteristics of the species formed by reaction of an indicator reagent with the analyte. These wavelengths require special lasers and are not transmitted well due to the absorption properties of the fibers. Additionally, the sensor stability is generally limited by the indicator. Since the detection mechanism requires photoexcitation, photodecomposition becomes an additional problem. Moreover, the associated dyes are usually unstable.

The use of a thin film as an optical waveguide is described in P. K. Tien, "Light Waves in Thin Films in Integrated Optics," Applied Optics, November 1971, vol. 10, no. 11, pp. 2395–2413, which is herein incorporated by reference. For a thin film to support propagating modes and act as a waveguide, its refractive index $n_r$ must be larger than the refractive indices of the material above and below it. The resonance condition in a rectangular waveguide is given by:

$$2kn_r t\cos\theta_r - 2\phi_{ru} - 2\phi_{rb} = 2m\pi$$

where k is the angular frequency of the light wave in the rectangular waveguide divided by the speed of light in a vacuum; t is the thickness of the waveguide; $\theta_r$ is the angle between the light path and the normal of the rectangular waveguide; $2\phi_{ru}$ is the phase change the wave suffers due to the total reflection at the upper film boundary and $2\phi_{rb}$ is the phase change the wave suffers due to the total reflection at the bottom film boundary (representing the Goos-Haenchen shifts); and m is an integer (0, 1, 2, 3, . . . ) representing the order of the mode. Thus the response changes with the thickness of the waveguide and the index of refraction.

The use of a thin film over a polished fiber as a filter is described in C. A. Millar, M. C. Brierley, & S. R. Mallinson, "Exposed-core single-mode-fiber channel-dropping filter using a high-index overlay waveguide," Optics Letters, April 1987, vol. 12, no. 4, pp. 284–86. The waveguide couples out light when its phase velocity matches the phase velocity of the fiber and the interaction length of the fiber-waveguide coupler equals the coupling length. An approximate calculation of the wavelength which will be coupled out is provided by the equation:

$$\lambda_m = (2t/m)(n_r^2 - n_{ef}^2)^{\frac{1}{2}}$$

where $n_{ef}$ is the fiber mode index of refraction.

SUMMARY OF THE INVENTION

An object of the invention is to provide a system for accurately detecting the presence and concentration of analytes in environmental matrices.

Another object of the invention is to provide a totally intrinsic sensor and thereby avoid the need to seal any optical cavity.

Another object of the invention is to provide a method for sensing analytes using a broadband source, thus allowing use of commercially accessible light emitting diodes.

Another object of the invention is to allow measurement of different analyte parameters by multiplexing multiple sensors.

The invention achieves the above objects by depositing a rectangular waveguide on a fiber field access block and using phase velocity matching conditions and spectral modulation techniques to optically detect changes in the rectangular waveguide as a result of interactions with the measurand. The term "measurand" is intended to encompass features which are capable of measurement using the present invention. Examples include analytes as well as physical properties such as temperature and pressure.

Briefly, in accordance with a preferred embodiment of the invention, an apparatus for detecting the presence of a measurand comprises a fiber field access block and a measurand sensitive layer overlying the fiber field access block. The fiber field access block has a clad fiber positioned such that a portion of the clad fiber is exposed to the measurand sensitive layer and the cladding, if any, on that portion of the fiber is of insufficient thickness to prevent an evanescent wave from escaping the fiber. Means are provided for detecting changes in the measurand sensitive layer caused by interaction with the measurand.

In accordance with another preferred embodiment of the invention, a method for detecting analytes comprises providing a fiber field access block having a clad fiber positioned in the fiber field access block such that a portion of the clad fiber is exposed to the outer surface of the fiber field access block and the cladding, if any, on that portion of the fiber is of insufficient thickness to prevent an evanescent wave from escaping the fiber. A measurand sensitive layer is applied over the outer surface of the fiber field access block. An optical source is coupled to one end of the clad fiber, and an optical detection component is coupled to either end of the clad fiber.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

DETAILED DESCRIPTION OF A PREFERRED EMBODIMENT OF THE INVENTION

Figure 1:
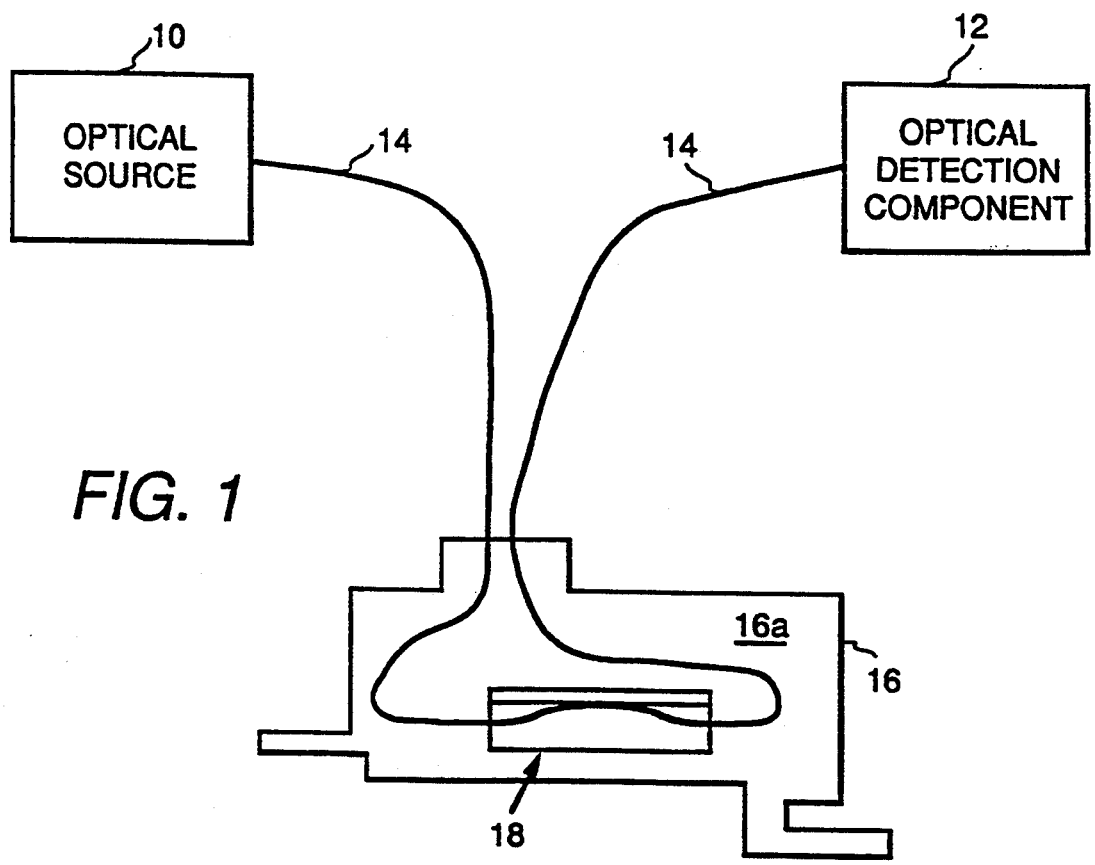
FIG. 1 is a schematic view of one embodiment of the invention including a fiber optic sensor in an environmental matrix, an optical source, and an optical detection component.

FIG. 1 is a schematic view of one embodiment of the invention including a fiber optic sensor 18 in an environmental matrix 16a contained in a test chamber 16, a fiber 14, an optical source 10, and an optical detection component 12. Environmental matrix 16a can be any type of environment where testing is desired, including, for example, air, water, and soil. Potential analytes which can be detected include, organic solvents, chlorinated hydrocarbons such as TCE (trichloroethylene), gasoline and fuel components, heavy metals such as Hg vapor, PCBs (polycholorinated biphenyls), and gases such as $H_2$ and $O_2$.

Figure 2A:
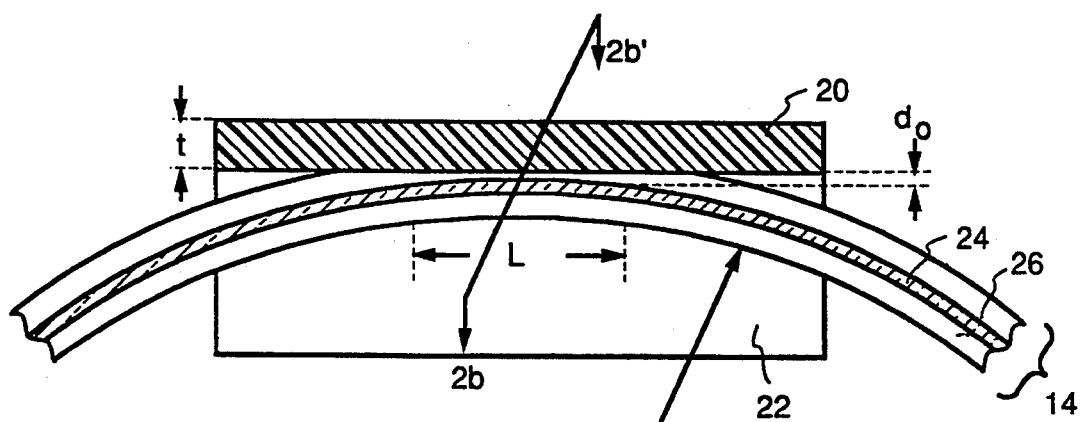
FIG. 2(a) is a sectional side view of a fiber optic sensor of the invention including a fiber field access block and a measurand sensitive layer.
Figure 2B:
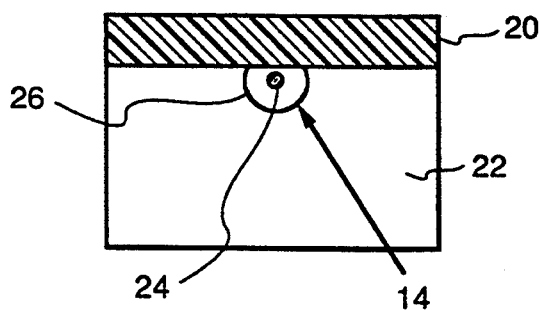
FIG. 2(b) is a sectional side view across the 2b-2b' plane of FIG. 2(a)

FIG. 2(a) is a sectional side view of a fiber optic sensor of the invention including a fiber field access block 22 and a measurand sensitive layer 20. FIG. 2(b) is a view across the 2b 2b' plane of FIG. 2(a). The absorption of an analyte into the measurand sensitive layer causes both swelling in the layer (so its physical thickness t increases) and alterations in the layer's index of refraction n (so its optical thickness, o=tn, changes). Physical properties such as temperature and pressure additionally result in changing physical and optical thicknesses. Fiber 14 has a core 24 comprising, for example, fused silica or fused silica with germanium covered by cladding 26 comprising, for example, a polymer or fused silica.

Fiber field access blocks are blocks with a groove and an optical fiber 14, inserted in the groove and polished such that a portion of the fiber, shown as L in FIG. 2(a), is exposed to an outer surface of the fiber field access block. The cladding, if any, on portion L of the fiber is thinner than the minimum thickness $d_0$ normally required to prevent the evanescent wave from escaping the fiber. Fiber field access blocks have part of the fiber cladding removed by controlled mechanical polishing along one side of the fiber. The fiber is first placed or mounted in a curved groove of radius R in a fused silica substrate, and bonded thereto. The substrate and fiber are then ground and polished until the desired cladding thickness (typically 1–2$\mu$m) remains. This reduced cladding of the fiber allows the evanescent field to interact with the measurand sensitive layer. Fiber field access blocks are commercially available from Sifam Ltd., Torquay, Devon, United Kingdom, and Canadian Instrumentation and Research Ltd. (CIR), Burlington, Ontario, Canada.

Measurand sensitive layer 20 forms a rectangular waveguide on top of the cylindrical waveguide formed by fiber 14. In one embodiment, measurand sensitive layer 20 is a crosslinked polymer chosen on the basis of its index of refraction as well as its absorption properties. The mechanism of swelling is altered by using polymeric layers of different crosslinking densities. The swelling can thus be adjusted between Fickian and Case-II behavior as discussed below. This behavior is different for different analytes, and thus significantly improves the specificity of the sensor.

The polymer material in this embodiment is chosen for its solubility in the presence of the analyte of interest before the crosslinking. The crosslinking density is then chosen to promote swelling and to prevent dissolution due to the permanent chemical interconnections resulting from crosslinking.

In one example, an epoxy resin is used as the polymer. One hundred parts of diglycidyl ether of bisphenol A and ten parts of diethylene triamene are mixed at mixing temperature Tm (typically 50° C.–70° C.). The mixture is then allowed to cure at temperature Tc (typically about 25° C.) for a period of time (typically 2–3 days). This procedure results in crosslinked glassy polymers. Different choices of Tm and Tc lead to different degrees of crosslinking resulting in different rates of penetration of analytes into the polymer.

A second example uses, as the polymer, gelatin mixed with ammonium dichromate at room temperature and baked at temperature Tc. Again, the choice of Tc provides different degrees of crosslinking. Several other examples include poly(chloroprene) solvent cast and baked at temperature Tc and styrene-butadiene-styrene copolymer solvent cast and baked at temperature Tc.

Preferably an adhesion promoter (not shown), such as, for example, a trimethoxsilane, is applied to the surface of the fiber field access block prior to application of measurand sensitive layer 20 by, for example, spin coating. The choice of adhesion promoter is strongly dependent on the material used for the measurand sensitive layer. Measurand sensitive layer 20 is typically two to ten microns thick and can be applied in any conventional manner, including spin coating, spray coating, and laminating. In one embodiment, the mixtures of the above examples are spin coated on the polished fiber field access blocks before being allowed to crosslink.

The well-known Fickian and Case-II swelling manifest themselves as follows on the measurand sensitive coating on the fiber field access block. In Fickian diffusion, the weight, as well as any linear dimension such as the width of the measurand sensitive layer, changes in proportion to $T^{178}$, where T represents the time that the sensor has been in the test chamber. In this case there is a gradient of concentration in absorbed volume. This Fickian diffusion is the normal, expected mode of diffusion. In Case-II swelling, the parameters vary in proportion to T, and there is a uniform concentration of analyte in absorbed volume. This essentially constitutes an abnormal diffusion. As the crosslinking densities are varied, the resulting behavior can be described as a function of time:

$$d \text{ is proportional to } T^{\alpha}, \alpha = \alpha(p_x), 1 \geq \alpha \geq \tfrac{1}{2}.$$

In this equation, d represents either the thickness t or the weight of the layer 20, and the exponent $\alpha$ is a function of the crosslinking density $P_x$. The dynamic behavior of the measurand sensitive layer can thus be changed by varying the crosslinking density $P_x$ as described in the examples above.

Linear non-crosslinked polymers can either enter into solution, remain unaffected, or swell, depending on the physical characteristics of the solvent these polymers are in contact with. In the case of methyl, ethyl, n-propyl, and iso-butyl alcohols, a special linear non-crosslinked polymer matrix such as poly(methyl methacrylate) can be used as the sensing polymer to detect these analytes without the need for crosslinking, because poly(methyl methacrylate) has a long chain that is capable of functioning in a similar manner as a crosslink.

Although the measurand sensitive layer has been discussed in the context of polymer films, the material of layer 20 is not limited to polymers. Any material which swells and has an index of refraction different from the index of refraction of glass can be used for layer 20 in the present invention. Examples include metals, such as gold, semiconductors such as silicon, and soft materials such as magnesium oxide.

Mechanically, the analyte sensitive layer is equivalent to an elastic material constrained in the plane of the rigid top surface of the fiber field access block. The stress-strain relationship, as described in I. S. Sokolnicoff, *Mathematical Theory of Elasticity*, chapters 3 and 5 (McGraw Hill, NY 1956), can be used to show that, when the layer swells, (a) the stress perpendicular to the layer is zero because the upper surface is not constricted and (b) the strain in the perpendicular direction depends strongly on Poisson's ratio for the sensitive layer and the volume fraction of analyte in the swollen layer. For polymeric layers, the Flory-Huggins theory (see, U. Eisele, *Introduction to Polymer Physics*, pp.161–64 (Springer-Verlag Berlin Heidelberg 1990)) and free energy equality can be used to show that the strain mentioned above is proportional to the concentration of the solvent in the environmental matrix.

The fiber supports at least one guided mode and the measurand sensitive layer supports several guided modes (i.e., allows certain wavelengths of light to be totally internally reflected). The coupling between the two waveguides is used to detect the measurand. Coupling occurs when the modes of the two waveguides exhibit the same phase velocity and thus depends on factors such as wavelength, the indexes of refraction for each waveguide, the distance of fiber exposed, electric field modes, and mismatch of propagation constants. The wavelengths which are coupled out dissipate in measurand sensitive layer 20, whereas the wavelengths which do not couple propagate through the fiber field access block to the optical detection component, resulting in a cone filter.

Figure 2C:
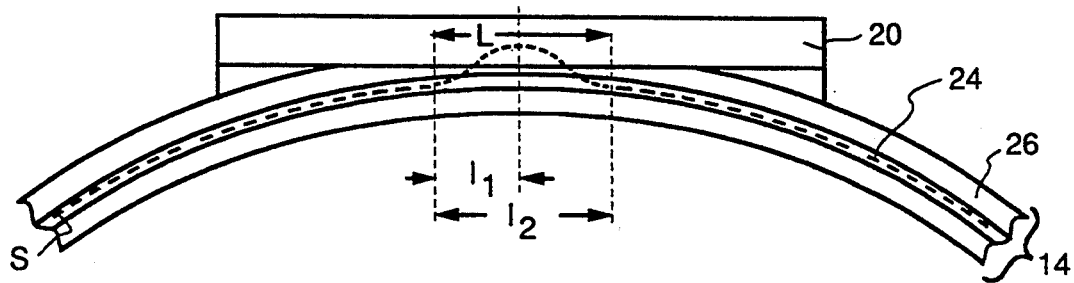
FIG. 2(c) is a sectional side view similar to that of FIG. 2(a) further showing a sample path of light and a recommended length of exposed fiber.

FIG. 2(c) is a sectional side view similar to that of FIG. 2(a) further showing a sample path of light and a recommended length L of exposed fiber 14. When light S (represented by the dashed line) travels in the fiber, the light is guided almost perfectly until the light enters the interaction region. Then the light energy is transferred to measurand sensitive layer 20 as per the phase matching condition described in aforementioned Millar et al., "Exposed-core single-mode-fiber channel-dropping filter using a high-index overlay waveguide."

If the interaction length equals $l_1$, most of the energy is transferred from the fiber into the measurand sensitive layer. Because the phase matching condition is symmetrical, the energy transfer is possible in both directions, and thus, if the interaction length is greater than $l_1$, some of the energy in the rectangular waveguide will be transferred back into fiber 14. Therefore, it is preferred that the interaction length be chosen to approximate $l_1$, so that the transfer of light into the measurand sensitive layer is maximized (thus enhancing the sensitivity of the sensor).

If the interaction length equals $l_2$ (a value twice that of $l_1$), then all of the light coupled into the measurand sensitive layer will be transferred back into the fiber. The length $l_2$, like the phase matching condition, is wavelength dependent. This dependence can be approximately expressed as:

$$l_2 = (\pi R a / v)^{\tfrac{1}{2}}$$

where R is the radius of the groove, a is the fiber core radius, and $v$ is one of the transverse mode parameters that are related by:

$$u^2 + v^2 = v^2$$

and $$v^2 = (2\pi a / \lambda)(n^2_{core} - n^2_{cladding})^{\tfrac{1}{2}}$$

where $\lambda$ is the wavelength, $n_{core}$ is the index of refraction of fiber core 24, and $n_{cladding}$ is the index of refraction of fiber cladding 26.

Figure 3A:
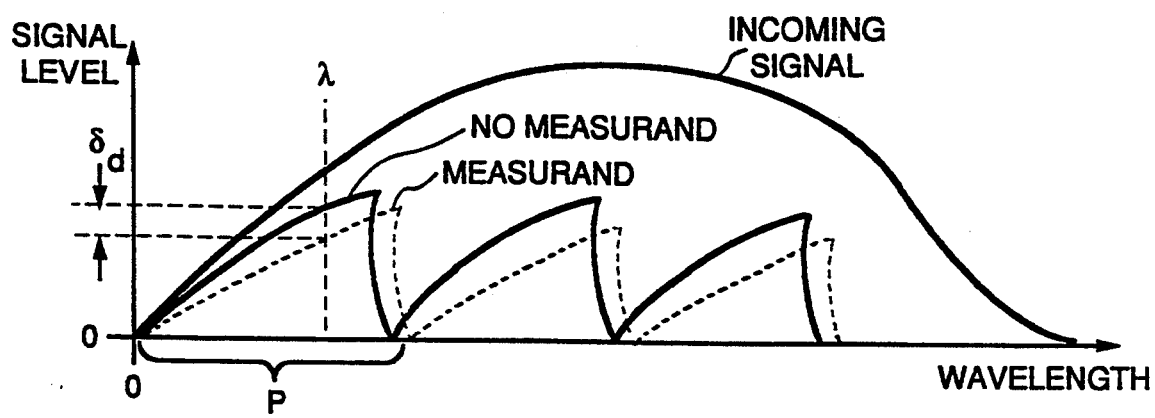
FIG. 3(a) is a graph illustrating an example of a spectral shift resulting from detection of a measurand.

Environmental changes are then detected by monitoring the spectral shifts (changes in the filtered signals) of the response of the sensor. FIG. 3(a) is a signal level vs. wavelength graph showing an input signal to the fiber access probe and several output signals, one (solid line) representing normal conditions and the other (dashed line) taken in the presence of a measurand. The average concentration of the measurand during a given time period p is determined by measuring the greatest difference $\delta_d$ between the normal signal and the signal in the presence of the measurand. This measurement is carried out easily, accurately, and inexpensively by a power measurement of a narrow wavelength range centered around $\lambda_o$ where the greatest difference $\delta_d$ occurs. This power reading is optionally ratioed with the result of an equivalent measurement around a point where the least difference occurs to provide robustness to source temperature, intensity and wavelength variations.

Figure 3B:
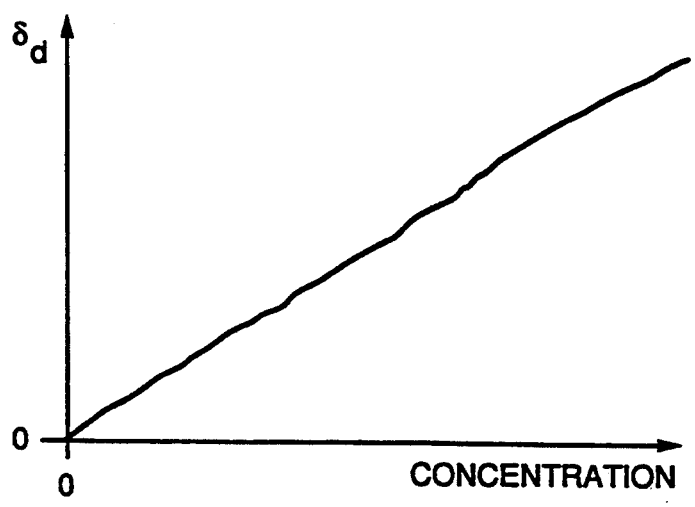
FIG. 3(b) is a graph illustrating a concentration curve for the measurand.

FIG. 3(b) is a signal level vs. wavelength graph of a concentration curve which corresponds to $\delta_d$. Data points on the concentration curve are obtained by supplying known concentrations or physical properties and measuring respective $\delta_d$s. After sufficient data points are obtained, a curve can be interpolated. Ideally the measurand sensitive material, thickness, and crosslinking properties will be selected so as to result in a straight line for the desired measurand, because the more linear the curve, the more precise the measurements. After the curve is graphed, an unknown concentration of a measurand can be determined by measuring $\delta_d$ and finding the corresponding concentration as indicated on the concentration curve.

Figure 4:
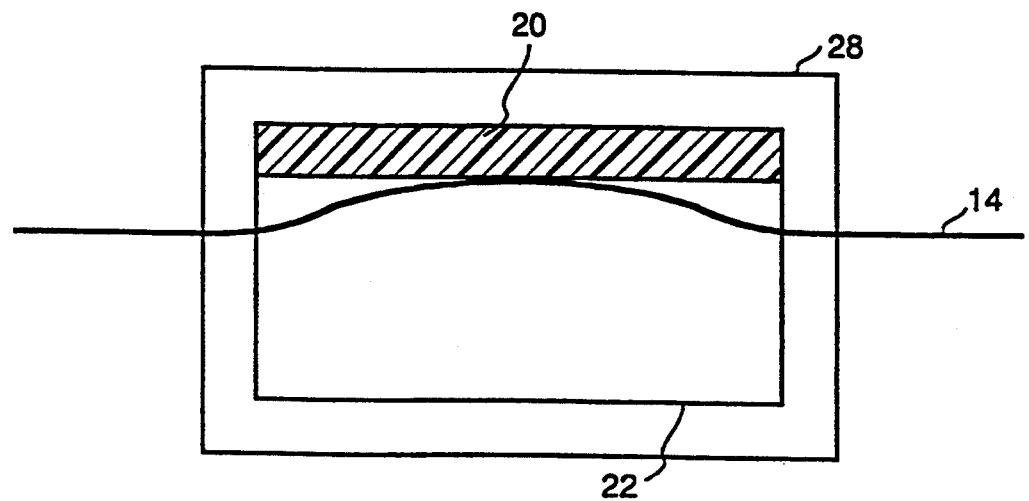
FIG. 4 is a schematic side view of a fiber optic sensor of the invention having an environmental cover.

FIG. 4 is a schematic side view of a fiber optic sensor having an environmental cover 28. The cover, which prevents contamination of the measurand sensitive layer, is useful for isolating a sensor from chemicals and the environment and measuring changes due solely to physical conditions. One example of an appropriate material for cover 28 is Teflon polytetrafluoroethylene, sold by E. I. Dupont de Nemours and Co. With this design, a sensor can be used to sense physical properties such as temperature and pressure without being affected by the properties of analytes.

Figure 5A:
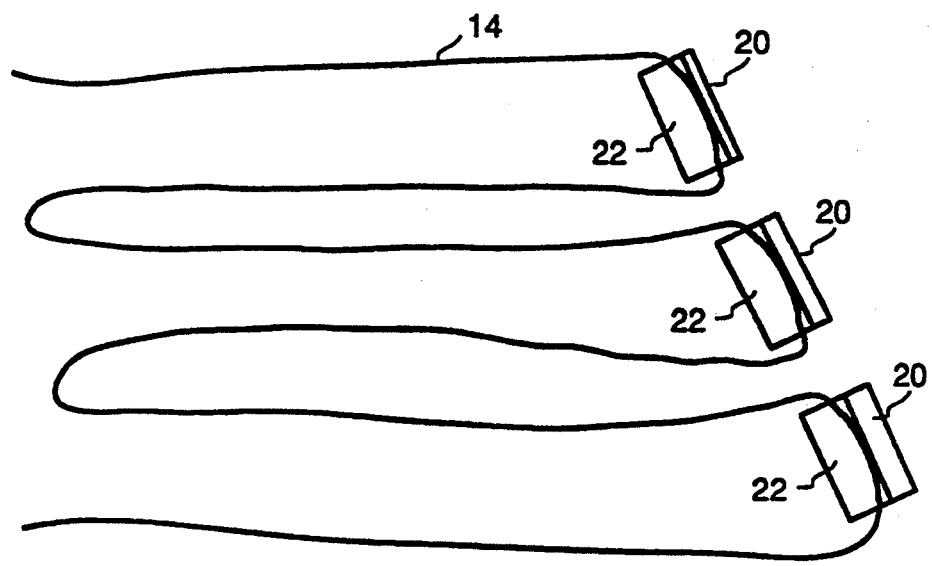
FIG. 5(a) is a schematic side view of three fiber optic sensors of the invention coupled in series.

FIG. 5(a) is a schematic side view of three fiber optic sensors coupled in series. An advantage of coupling the fiber optic sensors is that only one set of optical source and optical detection component is needed. Another advantage is that a fiber optic sensor can have a cover 28 (shown and discussed with respect to the embodiment of FIG. 4) which can be used to detect physical conditions and then compared with the signals of the other sensor or sensors, thus allowing analyte measurement which is not affected by changes in physical conditions.

Coupling in series can be accomplished, for example, by wavelength division multiplexing. For wavelength division multiplexing, each sensor is assigned a nonoverlapping wavelength range. One optical signal is supplied from the optical source to the sensors. Several methods are available for providing separate sensors with separate wavelength ranges. The method illustrated in FIG. 5(a) is that of using measurand sensitive layers of differing thicknesses. This thickness of the layer has a direct effect on the range of wavelengths that can be coupled out, and thus on which wavelengths will be transmitted through the fiber. An optical detection component (not shown) then demultiplexes (separates) the combined optical signals.

Figure 5B:
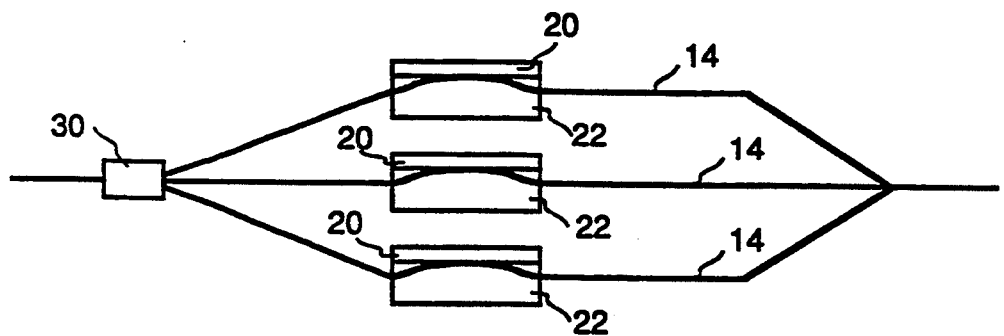
FIG. 5(b) is a schematic side view of three fiber optic sensors of the invention coupled in parallel.

FIG. 5(b) is a schematic side view of three fiber optic sensors coupled in parallel. A conventional time division or wavelength division multiplexer 30 can be used with this embodiment of the present invention. Or, as discussed with respect to the embodiments of FIGS. 5(a), 5(c), & 5(d), measurand sensitive layer thickness, exposed fiber length, measurand sensitive material, or crosslinking density variations can be used for multiplexing.

Figure 5C:
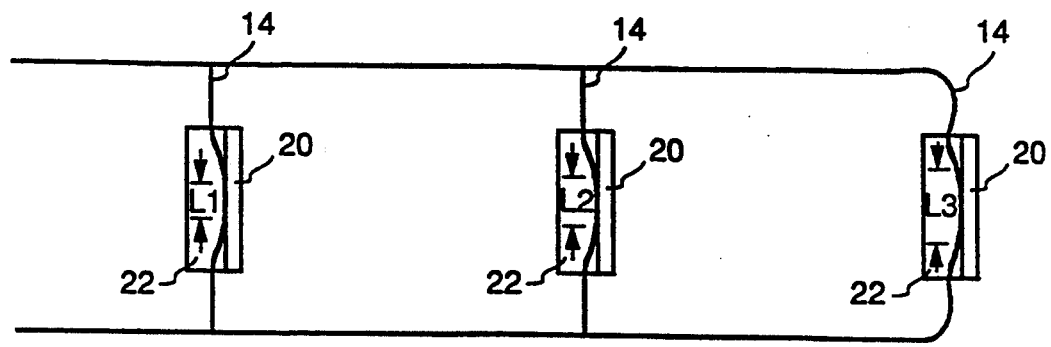
FIG. 5(c) is a schematic side view of three fiber optic sensors of the invention coupled in a ladder pattern.

FIG. 5(c) is a schematic side view of three fiber optic sensors coupled in a ladder pattern. The coupling is parallel, like that shown in FIG. 5(b), but because the lengths of fiber between each sensor and the source and detection component (not shown) are different, time division multiplexing is easily achieved. Additionally, in the embodiment of FIG. 5(c) there are different lengths (L1, L2, and L3) of fiber exposed to measurand sensitive layers 20. This factor can be used for wavelength division multiplexing because the varying lengths of fiber exposed to layer 20 affect the wavelengths at which a signal will be coupled into layer 20 from fiber 14.

Figure 5D:
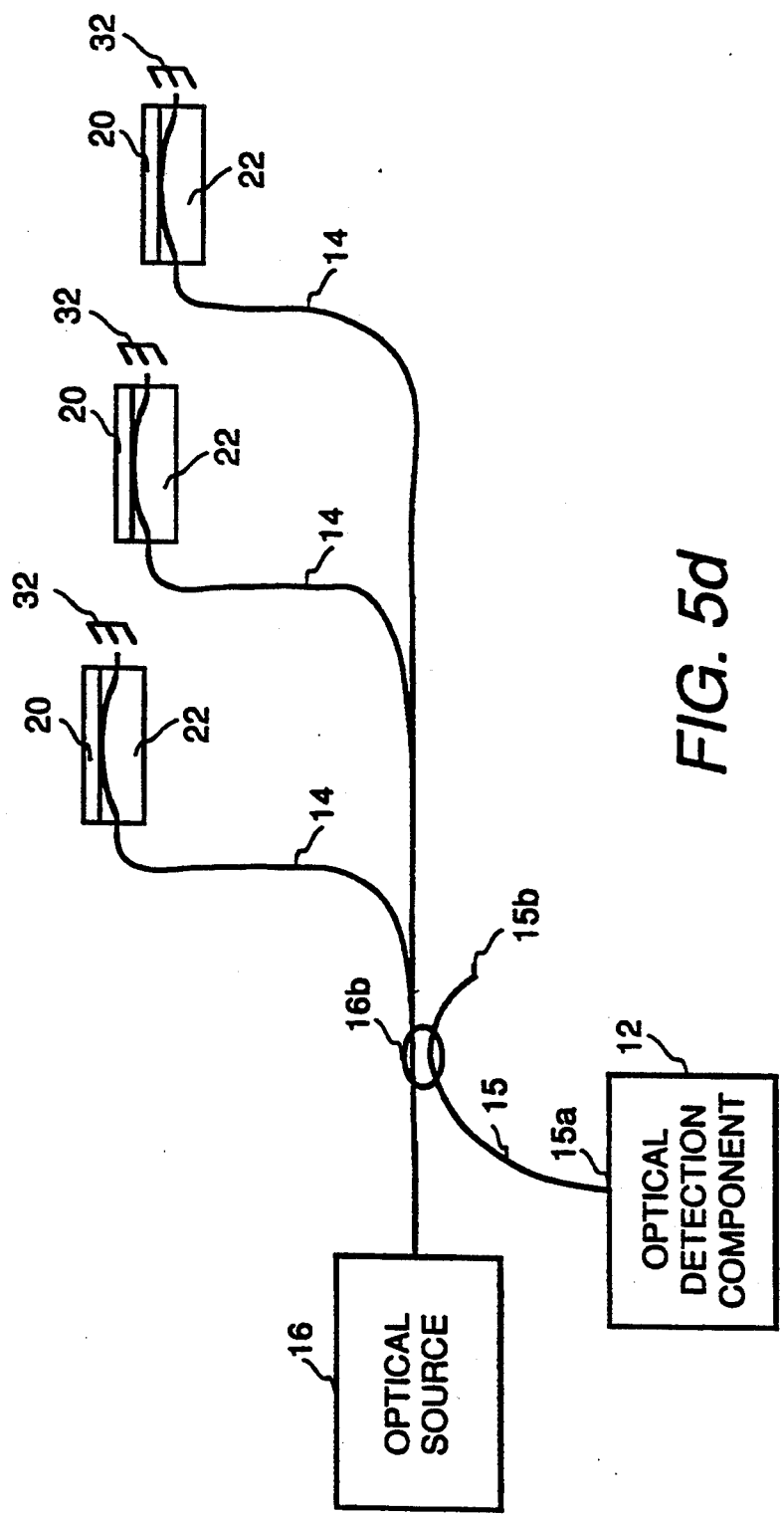
FIG. 5(d) is a schematic side view of three fiber optic sensors of the invention coupled in a reflective pattern.

FIG. 5(d) is a schematic side view of three fiber optic sensors coupled in a reflective pattern with reflectors 32. As in the embodiment of FIG. 5(c), the fiber lengths between the sensors and the source and detection component are different so time division multiplexing is available. One beneficial distinction of the configuration of FIG. 5(d) is that sensitivity is improved because the signal passes through the fiber optic sensor twice, once before reflection and once after reflection. The portion of the light which is reflected can be detected with detection component 12 by using a directional coupler 16b for reflected light to be coupled away from the source along a directional fiber 15 to one end 15a of fiber 15. In the preferred embodiment, the other end 15b of fiber 15 is either crushed or coated with an index matching gel, for example, so that no light is reflected from end 15b to end 15a. A reflector and directional coupler can also be used with a single sensor, if desired.

Even if the lengths of fibers were the same, wave division multiplexing can be achieved by using different measurand sensitive materials (which thus have different indices of refraction) or by using different degrees of crosslinking, both of which affect the wavelengths at which a signal will be coupled into layer 20 from fiber 14.

Another option is to use a combination of the variables of measurand sensitive layer thickness, exposed fiber length, measurand sensitive layer material, and degree of crosslinking. When determining these variables, the nature of the measurand must be considered. In the preferred embodiment the variables are chosen so that the concentration curve of FIG. 3(b) is as linear as possible.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An apparatus for detecting presence of a measurand, comprising:
   a fiber field access block;
   a measurand sensitive layer overlying said fiber field access block; and
   means for detecting changes in a parameter selected from the group of thickness and index of refraction of said measurand sensitive layer caused by interaction with said measurand; and
   wherein said fiber field access block has a clad fiber positioned such that a portion of said fiber is exposed to said measurand sensitive layer and any cladding on said portion of said fiber is thinner than required to prevent an evanescent wave from escaping said fiber.

2. The apparatus of claim 1, wherein said measurand sensitive layer comprises a crosslinked polymer including a degree of crosslinking and a material selected to correspond to a particular measurand.

3. The apparatus of claim 2, wherein said crosslinked polymer layer comprises one of the group consisting of poly(chloroprene), styrene-butadiene-styrene copolymer, gelatin, and diethylene triamene.

4. The apparatus of claim 1, wherein said measurand sensitive layer comprises a linear non-crosslinked polymer.

5. The apparatus of claim 1, wherein said measurand sensitive layer comprises polymethylmethacrylate.

6. The apparatus of claim 1, wherein said measurand sensitive layer comprises material selected from the group consisting of silicon and magnesium oxide.

7. The apparatus of claim 1, further including:
   an optical source coupled to one end of said clad fiber;
   a reflector for reflecting light from the other end of said clad fiber back into said clad fiber;
   a directional fiber;
   a directional coupler for coupling said directional fiber to the portion of said clad fiber situated between said optical source and said fiber field access block; and
   an optical detection component coupled to said directional fiber for measuring light reflected by said reflector.

8. The apparatus of claim 1, further including:
   an optical source coupled to one end of said clad fiber; and
   an optical detection component coupled to the other end of said clad fiber for measuring spectral shifts in the output signal caused by coupling of different wavelengths between said fiber and said measurand sensitive layer.

9. The apparatus of claim 1, further including a cover enclosing said measurand sensitive layer for preventing contamination of said measurand sensitive layer.

10. The apparatus of claim 9, wherein said cover comprises polytetrafluoroethylene.

11. The apparatus of claim 1, wherein said fiber field access block and said measurand sensitive layer comprise a first fiber field access block and a first measurand sensitive layer, respectively, and further comprising:
    a second fiber field access block; and
    a second measurand sensitive layer overlying said second fiber field access block;
    wherein said second fiber field access block has a second clad fiber positioned such that a portion of said second fiber is exposed to said second measurand sensitive layer and any cladding on said portion of said second fiber is thinner than required to prevent an evanescent wave from escaping said second fiber;
    wherein said first fiber field access block and said second fiber field access block are optically coupled together; and
    wherein said first fiber field access block and said first measurand sensitive layer differ from said second fiber field access block and said second measurand sensitive layer in a feature selected from the group consisting of length of portion of fiber exposed to said measurand sensitive layer, thickness, material, and degree of crosslinking of said measurand sensitive layer.

12. The apparatus of claim 11, wherein said first and second fiber field access blocks are optically coupled together in one configuration selected from the group consisting of series, parallel, ladder, and reflective.

13. The apparatus of claim 1, wherein said fiber field access block, said clad fiber, and said measurand sensitive layer comprise a first fiber field access block, a first clad fiber, and a first measurand sensitive layer, respectively, and further comprising:
    a second fiber field access block; and
    a second measurand sensitive layer overlying said second fiber field access block;
    wherein said second fiber field access block has said first clad fiber positioned such that a portion of said first clad fiber is exposed to said second measurand sensitive layer and any cladding on said portion of said first clad fiber is thinner than required to prevent an evanescent wave from escaping said first clad fiber;
    wherein said first fiber field access block and said first measurand sensitive layer differ from said second fiber field access block and said second measurand sensitive layer in a feature selected from the group consisting of length of portion of fiber exposed to said measurand sensitive layer, thickness, material, and degree of crosslinking of said measurand sensitive layer.

14. A method for detecting analytes, comprising the steps of:
    providing a fiber field access block having a clad fiber positioned in said fiber field access block such that a portion of said fiber is exposed to an outer surface of said fiber field access block and any cladding on said portion of said fiber is thinner than required to prevent an evanescent wave from escaping said fiber;
    applying a measurand sensitive layer over said outer surface of said fiber field access block;
    positioning said fiber field access block in an environmental matrix;
    providing an optical signal through said fiber; and
    measuring an optical signal produced from said fiber.

15. The method of claim 14, wherein said fiber field access block and said measurand sensitive layer comprise a first fiber field access block and a first measurand sensitive layer, respectively, and further comprising, prior to the step of providing said optical signal, the steps off
    providing a second fiber field access block having a second clad fiber positioned in said second fiber field access block such that a portion of said second fiber is exposed to an outer surface of said second fiber field access block and any cladding on said portion of said second fiber is thinner than required to prevent an evanescent wave from escaping said second fiber;
    applying a second measurand sensitive layer overlying said outer surface of said second fiber field access block; positioning said second fiber field access block in said environmental matrix; and
    optically coupling said first and second fiber field access blocks; and
    wherein said first fiber field access block and said first measurand sensitive layer differ from said second fiber field access block and said second measurand sensitive layer in a feature selected from the group consisting of length of portion of fiber exposed to said measurand sensitive layer, thickness, material, and degree of crosslinking of said measurand sensitive layer.

16. The method of claim 15, wherein said first and second fiber field access blocks are optically coupled together in one configuration selected from the group consisting of series, parallel, ladder, and reflective.

17. The method of claim 15, further including the steps of:

enclosing one of said first and second fiber field access blocks with a cover for preventing contamination prior to providing said optical signal;

measuring the optical signal produced from said second fiber after providing said optical signal; and comparing the optical signals produced by said first and second fibers.

18. The method of claim 14, wherein said fiber field access block, said clad fiber, and said measurand sensitive layer comprise a first fiber field access block, a first clad fiber, and a first measurand sensitive layer, respectively, and further comprising, prior to the step of providing said optical signal, the steps of:

providing a second fiber field access block having said first clad fiber positioned in said second fiber field access block such that a portion of said first clad fiber is exposed to an outer surface of said second fiber field access block and any cladding on said portion of said first clad fiber is thinner than required to prevent an evanescent wave from escaping said first clad fiber;

applying a second measurand sensitive layer overlying said outer surface of said second fiber field access block;

positioning said second fiber field access block in said environmental matrix; and wherein said first fiber field access block and said first measurand sensitive layer differ from said second fiber field access block and said second measurand sensitive layer in a feature selected from the group consisting of length of portion of fiber exposed to said measurand sensitive layer, thickness, material, and degree of crosslinking of said measurand sensitive layer.

* * * * *